United States Patent [19]
Lin

[11] Patent Number: 5,716,416
[45] Date of Patent: Feb. 10, 1998

[54] ARTIFICIAL INTERVERTEBRAL DISK AND METHOD FOR IMPLANTING THE SAME

[76] Inventor: Chih-I Lin, 14292 Spring Vista Lane, Chino Hills, Calif. 91709

[21] Appl. No.: 711,589

[22] Filed: Sep. 10, 1996

[51] Int. Cl.⁶ .................................................... A61F 2/44
[52] U.S. Cl. ................................................ 623/17; 606/61
[58] Field of Search .......................... 623/16, 17, 18, 623/66; 606/61

[56] References Cited

U.S. PATENT DOCUMENTS

| | | | |
|---|---|---|---|
| 5,171,280 | 12/1992 | Baumgartner | 623/17 |
| 5,192,326 | 3/1993 | Bao et al. | 623/17 |

Primary Examiner—David J. Isabella
Attorney, Agent, or Firm—Bacon & Thomas

[57] ABSTRACT

A ring-shaped artificial intervertebral disk is made of an elastic material implantable into the human body. The artificial intervertebral can be transformed mechanically to have a straight rod shape before being implanted. Upon being implanted into the vertebrae, the artificial intervertebral disk regains its original ring shape.

15 Claims, 4 Drawing Sheets

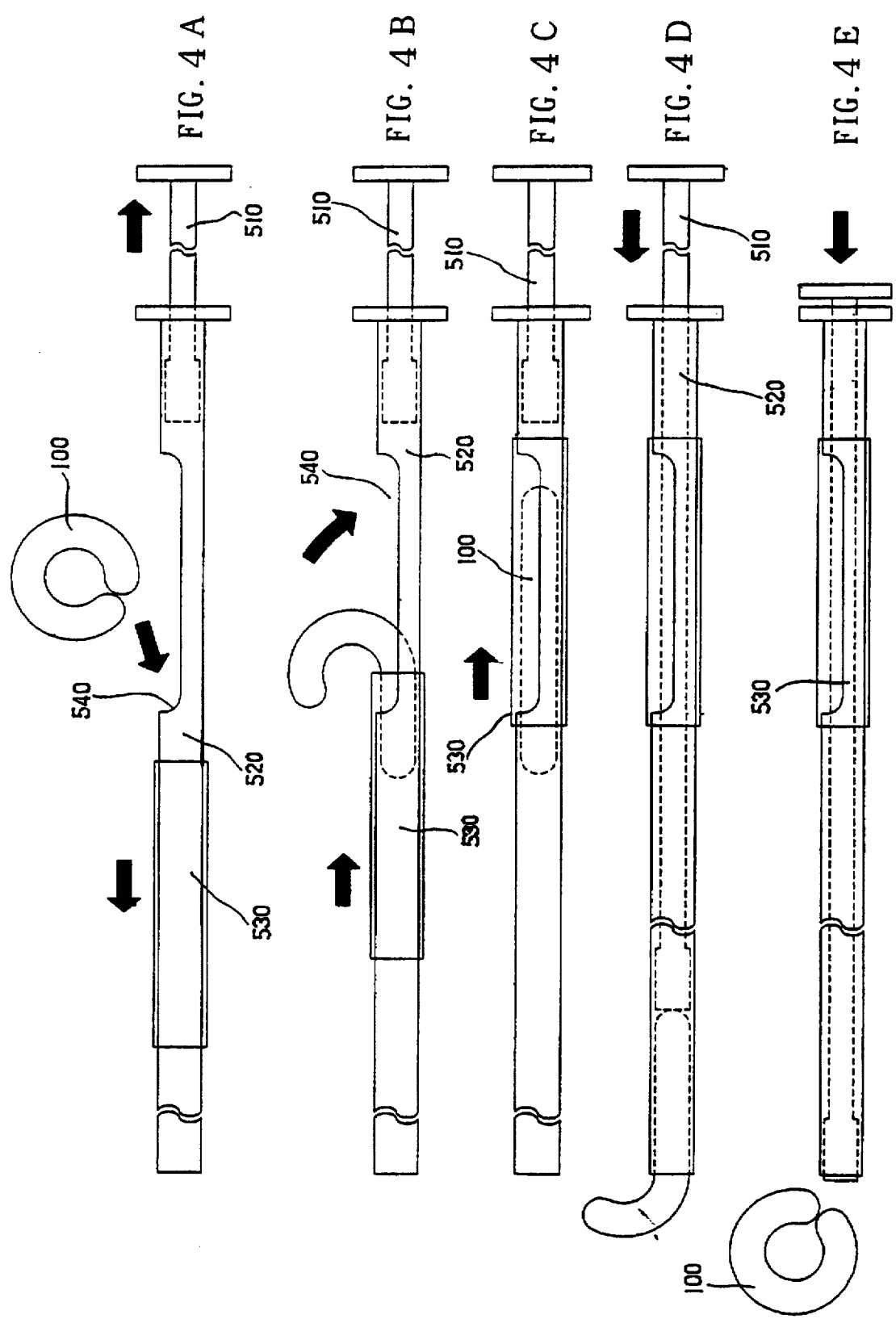

or a fiber material. As shown in FIG. 1A or 1B, the elastic material referred to above is covered with a protective layer of silicone or hydrogel for preventing the elastic material from making direct contact with the vertebrae. The direct contact of the elastic material with the vertebrae can hurt the vertebrae. As shown in FIG. 1A, the artificial intervertebral disk of the present invention is composed of an inner ring of stainless steel 316 LVM and an outer layer of silicone. As shown in FIG. 1B, the artificial intervertebral disk of the present invention is composed of an inner ring-shaped spring of a titanium-based alloy, and an outer layer of

ARTIFICIAL INTERVERTEBRAL DISK AND METHOD FOR IMPLANTING THE SAME

FIELD OF THE INVENTION

The present invention relates generally to a surgical treatment of an injured intervertebral disk, and more particularly to a artificial intervertebral disk for use in the surgical treatment of an injured or defective intervertebral disk.

BACKGROUND OF THE INVENTION

The conventional artificial intervertebral disk is generally composed of a hollow cylindrical body having a perforated periphery, and of bone grafts contained in the cylindrical body. The artificial intervertebral disk disclosed in the U.S. Pat. No. 4,501,269 is a case in point. In addition, there is a similar product called BAK™ Interbody Fusion System, which is in fact a refined product made by the Spintech Corp. of the United States on the basis of the claimed invention disclosed in the U.S. Pat. No. 5,015,247. Such conventional artificial intervertebral disks as mentioned above are large in volume and are therefore not suitable for use in treating an injured intervertebral disk by a discatomy in conjunction with an endoscope.

SUMMARY OF THE INVENTION

It is therefore the primary objective of the present invention to provide an artificial intervertebral disk which can be implanted directly by an implantation method making use of an endoscope.

It is another objective of the present invention to provide an implantation method for implanting an artificial intervertebral disk.

Prior to a surgical operation, the artificial intervertebral disk of the present invention is first deformed mechanically so as to have a barlike form. As a result, the artificial intervertebral disk of the present invention can be implanted immediately after the completion of the surgical removal of the intervertebral disk by the endoscopic discatomy. Upon completion of the implantation of the barlike intervertebral disk of the present invention, the barlike artificial intervertebral disk of the present invention is capable of transforming automatically into a ring-shaped intervertebral disk having an opening. The rehabilitation of the endoscopic implantation of the artificial intervertebral disk of the present invention is relatively faster in view of the fact that the employment of an endoscope enables an operating surgeon to attain the surgical implantation by making a relatively small incision which heals faster.

A method for implanting the present artificial intervertebral disk comprises the following steps:

inserting a hollow tube into a body of a patient receiving treatment from an incision thereof so that a first opening end of said hollow tube reaches a space created by removing an injured or deformed intervertebral disk of said patient and a second opening end of said hollow tube is protruding outwardly from said body;

transforming said artificial intervertebral disk by an external force to have a straight rod shape or a shape similar to said straight rod shape;

inserting said artificial intervertebral disk into said hollow tube from said second opening end and pushing said transformed artificial intervertebral disk so that said transformed artificial intervertebral disk exits from said first opening end of said hollow tube; and withdrawing said hollow tube from said body while said transformed artificial intervertebral disk regains its ring-shaped profile in said space.

The foregoing objectives, features and advantages of the present invention will be more readily understood upon a thoughtful deliberation of the following detailed description of embodiments of the present invention in conjunction with the accompanying drawings.

BRIEF DESCRIPTION OF THE DRAWINGS

FIGS. 4A–4E are schematic views illustrating the mechanical implantation of the artificial intervertebral disk of the present invention.

DETAILED DESCRIPTION OF THE PREFERRED EMBODIMENTS

The artificial intervertebral disk of the present invention is made of a material having a considerable degree of elasticity. In addition, the artificial intervertebral disk of the present invention has a ring-shaped profile with an opening. The artificial intervertebral disk of the present invention is characterized in that it can be transformed by an external force so as to have a straight rod shape or a form similar to the straight rod shape before it is implanted intervertebrally, and that it is capable of returning to its original ring form after being implanted intervertebrally.

Figure 1:
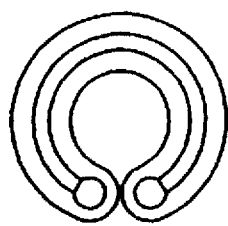
FIGS. 1A–1F are schematic views of six embodiments of the present invention.
Figure 1:
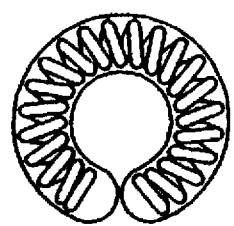
Figure 1:
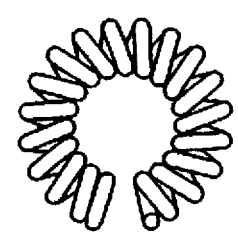
Figure 1:
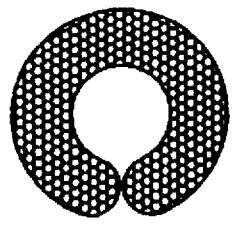
Figure 1:
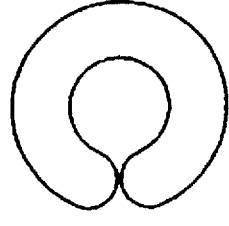
Figure 1:
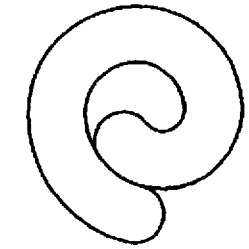

In other words, the artificial intervertebral disk of the present invention is not a closed ring. Two open ends of the ring-shaped disk of the present invention encircle the ring center for 300 degrees or so. For example, the open ends of the artificial intervertebral disks of the present invention encircle together the ring center for 360 degrees, as shown in FIGS. 1A, 1B, 1D, and 1E. Another artificial intervertebral disk of the present invention has open ends which encircle the ring center for about 340 degrees, as shown in FIG. 1C. An artificial intervertebral disk, as shown in FIG. 1F, has open ends encircling the ring center for about 420 degrees. Generally speaking, the disk having the encircling degree greater than 330 is desirable while the disk having the encircling degree of 360 or more is most desirable.

The artificial intervertebral disk of the present invention is made of the elastic material which is implantable. As shown in FIG. 1C, the artificial intervertebral disk of the present invention is made of a ring-shaped spring of a stainless steel 316 LVM, a titanium-based material such as Ti-6-4, an alloy material made of cobalt, molybdenum and nickel, or a fiber material. As shown in FIG. 1A or 1B, the elastic material referred to above is covered with a protective layer of silicone or hydrogel for preventing the elastic material from making direct contact with the vertebrae. The direct contact of the elastic material with the vertebrae can hurt the vertebrae. As shown in FIG. 1A, the artificial intervertebral disk of the present invention is composed of an inner ring of stainless steel 316 LVM and an outer layer of silicone. As shown in FIG. 1B, the artificial intervertebral disk of the present invention is composed of an inner ring-shaped spring of a titanium-based alloy, and an outer layer of silicone. Both disks of FIGS. 1A and 1B have an encircling angle of 360 degrees. As shown in FIG. 1D, the artificial intervertebral disk of the present invention is composed of an outer layer of polyethylene (PE) knitted bag and elastic particles filled in the bag, with the encircling angle being about 360 degrees. Said PE knitted bag may be replaced by a deformable container. The elastic particles may be hydrogel or high density polyethylene (HDPE) particles. The hydrogel particles inside the bag are capable of being exerted on evenly by an external force. In addition, the water contained in the hydrogel particles can be released evenly. Moreover, the hydrogel particles are capable of absorbing the water of the body fluid when the external force is relaxed or released. As shown in FIG. 1E, the artificial intervertebral disk of the present invention is made of hydrogel, with the encircling angle being about 360 degrees. As shown in FIG. 1F, the artificial intervertebral disk of the present invention is made of hydrogel, with the encircling angle being about 420 degrees. Generally speaking, the artificial intervertebral disk containing the hydrogel particles is most desirable in view of the functional advantages of hydrogel particles as described above. The hydrogel particles or hydrogel material used in the artificial intervertebral disks are saturated with water prior to implantation.

Figure 2:
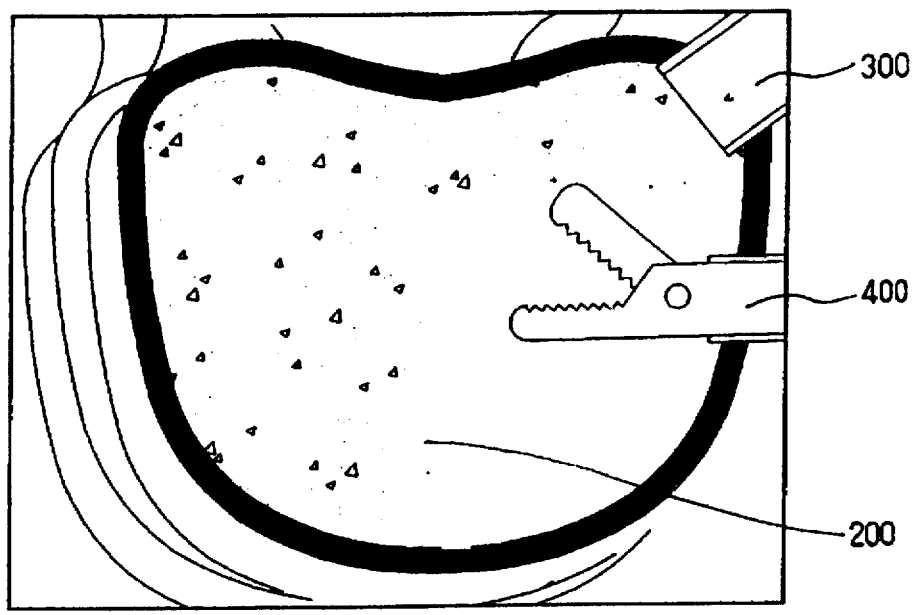
FIGS. 2A–2C are schematic views illustrating the implantation of the artificial intervertebral disk of the present invention.
Figure 2:
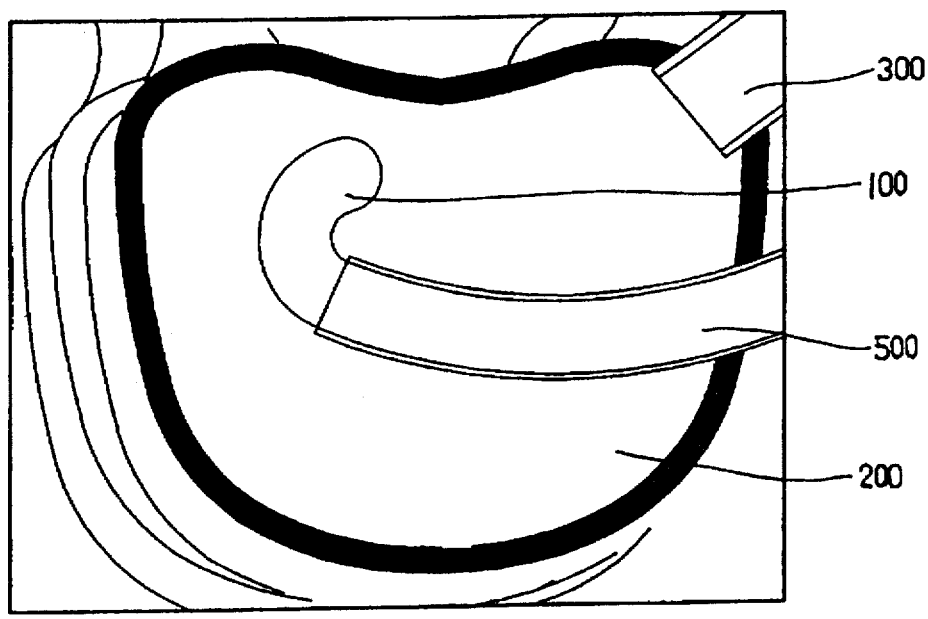
Figure 2C:
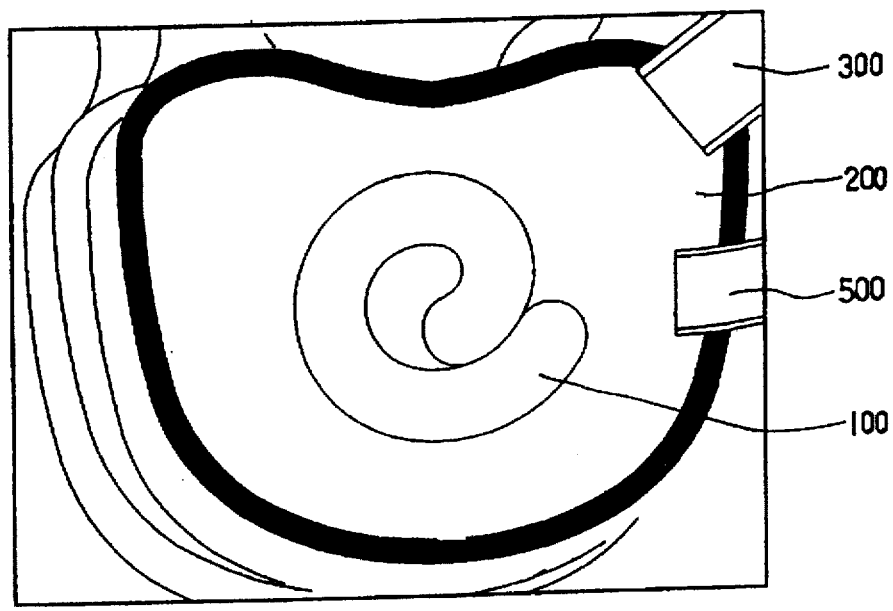

The process of implanting the artificial intervertebral disk of the present invention is illustrated in FIGS. 2A–2C. As shown in FIG. 2A, a clamping and removing tool 400 is used to remove the injured or deformed intervertebral disk 200 in conjunction with an endoscope 300. As shown in FIG. 2B, an artificial intervertebral disk 100 of the present invention is implanted by an implantation tool 500 in conjunction with the endoscope 300. The function of the intervertebral disk 200 is carried out by the implanted artificial intervertebral disk 100 of the present invention. As shown in FIG. 2C, the implanted artificial intervertebral disk 100 has regained its original ring shape with an opening. If necessary, an adjusting tool may be used to help the implanted artificial intervertebral disk 100 regain its original shape.

Figure 3:
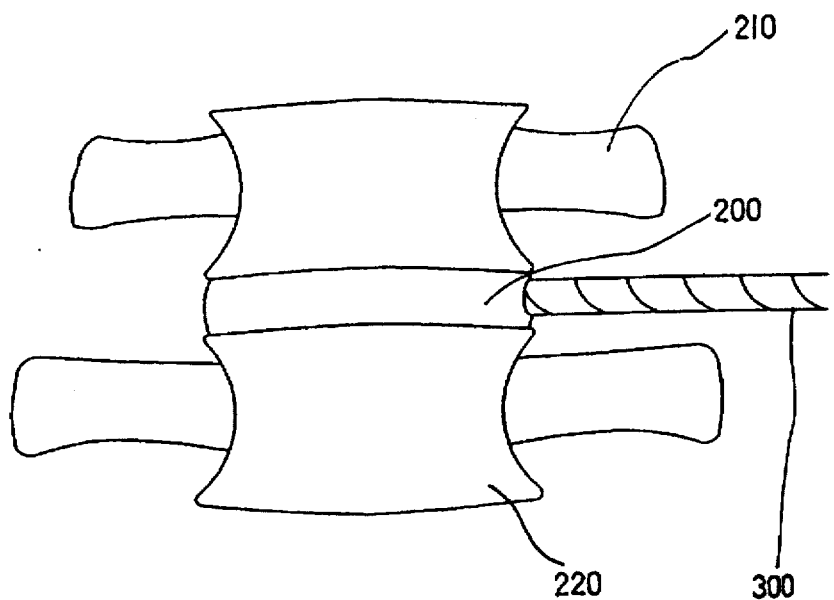
FIG. 3 is a schematic view illustrating the surgical implantation of the artificial intervertebral disk of the present invention by the endoscopic discatomy.

The surgical operation for implanting the artificial intervertebral disk 100 of the present invention is also illustrated in FIG. 3, in which the reference numerals of 200 and 300 are similar in definition to the like reference numerals of FIG. 2B, and reference numerals of 210 and 220 represent vertebrae. The endoscope 300 may be located in a hollow tube in which the clamping and removing tool 400 and/or the implantation tool 500 shown in FIGS. 2A and 2B, are inserted in sequence.

As shown in FIGS. 4A–4E, the artificial intervertebral disk 100 of the present invention is implanted by the implantation tool. It is shown in FIG. 4A that the artificial intervertebral disk 100 is first inserted into the implantation tool. Before the disk 100 is inserted, the press device 510 of the implantation tool must be pulled out in the direction indicated by an arrow while the sleeve 530 of the implantation tool is pulled in the direction opposite to the direction in which the press device 510 is pulled. As a result, the opening 540 of the cavity 520 is emerged. As shown in FIG. 4B, the disk 100 is inserted into the cavity 520 of the implantation tool via the opening 540 before the sleeve 530 is pushed in the direction indicated by an arrow such that the disk 100 is entirely received in the cavity 520 and that the disk 100 is covered by the sleeve 530, as shown in FIG. 4C. Thereafter, the press device 510 is pushed in the direction indicated by an arrow so as to force out the disk 100, as shown in FIG. 4D. Now referring to FIG. 4E, the disk 100 regains its original shape after being forced out of the implantation tool.

The embodiments of the present invention described above are to be regarded in all respects as being merely illustrative and not restrictive. Accordingly, the present invention may be embodied in other specific forms without deviating from the spirit thereof. The present invention is therefore to be limited only by the scopes of the following appended claims.

What is claimed is:

1. An artificial intervertebral disk for surgical implantation in a defective natural intervertebral disk, the artificial intervertebral disk comprising an elastic material having an annular configuration at least substantially enclosing a central opening wherein the artificial intervertebral disk is deformed by an external force applied during implantation into a substantially straight configuration and wherein the artificial intervertebral disk returns to its annular configuration upon removal of the external force after implantation.

2. The artificial intervertebral disk as defined in claim 1, wherein said annular configuration has an encircling angle of at least 340 degrees.

3. The artificial intervertebral disk as defined in claim 1, wherein said annular configuration has an encircling angle of at least 360 degrees.

4. The artificial intervertebral disk as defined in claim 1, wherein said artificial intervertebral disk comprises a spring body implantable into a human body.

5. The artificial intervertebral disk as defined in claim 1, wherein said artificial intervertebral disk is made of a hydrogel material.

6. The artificial intervertebral disk as defined in claim 1, wherein said disk is made of stainless steel 316 LVM.

7. The artificial intervertebral disk as defined in claim 1, wherein said artificial intervertebral disk comprises an inner body covered by an outer layer.

8. The artificial intervertebral disk as defined in claim 7, wherein said inner body comprises stainless steel 310 LVM; and wherein said outer layer comprises a hydrogel material.

9. The artificial intervertebral disk as defined in claim 7, wherein said inner body comprises a titanium-based alloy; and wherein said outer layer comprises a hydrogel material.

10. The artificial intervertebral disk as defined in claim 7, wherein said inner body comprises a plurality of hydrogel particles; and wherein said outer layer comprises a deformable container.

11. The artificial intervertebral disk as defined in claim 10, wherein said deformable container comprises a polyethylene knitted bag.

12. The artificial intervertebral disk as defined in claim 1 wherein said disk is made of a silicone material.

13. The artificial intervertebral disk as defined in claim 7 wherein said inner body comprises stainless steel 310 LVM, and wherein said outer layer comprises a silicone material.

14. The artificial intervertebral disk as defined in claim 7 wherein said inner body comprises a titanium-based alloy and wherein said outer layer comprises a silicone material.

15. A method for implanting an artificial intervertebral disk comprising the following steps:

making an incision in a body of a patient receiving treatment;

removing an injured or deformed intervertebral disk creating a space;

inserting a hollow tube into the body through the incision therein so that a first opening end of said hollow tube reaches the space created by removal of the injured or deformed intervertebral disk of said patient and a second opening end of said hollow tube is protruding outwardly from said body;

applying an external force to an artificial intervertebral disk normally having an annular configuration at least substantially enclosing a central opening such that the artificial intervertebral disk has a straight configuration;

inserting said straightened artificial intervertebral disk into said hollow tube from said second opening end and pushing said straightened artificial intervertebral disk so that said straigtened artificial intervertebral disk exists from said first opening end of said hollow tube into said space; and withdrawing said hollow tube from said body thereby removing the external force from the artificial intervertebral disk and returning the artificial intervertebral disk to the annular configuration in said space.

\* \* \* \* \*